US010010707B2

(12) United States Patent
Colburn et al.

(10) Patent No.: US 10,010,707 B2
(45) Date of Patent: Jul. 3, 2018

(54) INTEGRATED MICRONEEDLE ARRAY DELIVERY SYSTEM

(71) Applicant: 3M INNOVATIVE PROPERTIES COMPANY, St. Paul, MN (US)

(72) Inventors: David J. Colburn, Lake Elmo, MN (US); Erik J. Johnson, Cohasset, MN (US); David H. Brandwein, St. Paul, MN (US); Jerome E. Gysbers, Minneapolis, MN (US); Patrick J. Young, Minneapolis, MN (US); Adam S. Cantor, River Falls, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 905 days.

(21) Appl. No.: 14/350,156

(22) PCT Filed: Oct. 9, 2012

(86) PCT No.: PCT/US2012/059273
§ 371 (c)(1),
(2) Date: Apr. 7, 2014

(87) PCT Pub. No.: WO2013/055638
PCT Pub. Date: Apr. 18, 2013

(65) Prior Publication Data
US 2014/0257187 A1 Sep. 11, 2014

Related U.S. Application Data

(60) Provisional application No. 61/546,340, filed on Oct. 12, 2011.

(51) Int. Cl.
*A61M 37/00* (2006.01)

(52) U.S. Cl.
CPC . *A61M 37/0015* (2013.01); *A61M 2037/0023* (2013.01); *A61M 2037/0046* (2013.01)

(58) Field of Classification Search
CPC ...... A61M 37/0015; A61M 2037/0023; A61M 2037/0046; A61M 5/1428; A61M 2005/14252; A61M 2005/1585
See application file for complete search history.

(56) References Cited

U.S. PATENT DOCUMENTS 6,091,975 A    7/2000  Daddona et al.
6,219,574 B1   4/2001  Cormier et al.
(Continued)

FOREIGN PATENT DOCUMENTS

AU    2005200910    3/2005
EP    1 229 304     8/2002
(Continued)

OTHER PUBLICATIONS

Brochure from GE Healthcare entitled "Hospital Operations Management"; [retrieved from the internet on Mar. 19, 2014] 19 pgs. available at http://www.3.gehealthcare.com/en/Services/Hospital_Operations_Management.
(Continued)

*Primary Examiner* — Laura Bouchelle

(57) ABSTRACT

The present disclosure provides a low-profile system and methods for delivering a microneedle array. The delivery system includes a housing that may be secured to and temporarily worn on a patient's skin. A carrier assembly coupled to a microneedle array is received in the housing proximate an applicator device. The carrier assembly is at least releasably secured to the housing and it is typically not attached or otherwise fixed to any portion of the applicator device.

40 Claims, 10 Drawing Sheets

(56) References Cited

U.S. PATENT DOCUMENTS

| | | | |
|---|---|---|---|
| 6,312,612 | B1 | 11/2001 | Sherman et al. |
| 6,743,211 | B1 | 6/2004 | Prausnitz et al. |
| 6,830,562 | B2 | 12/2004 | Mogensen et al. |
| 6,881,203 | B2 | 4/2005 | Delmore et al. |
| 7,004,928 | B2 | 2/2006 | Aceti et al. |
| 7,097,631 | B2 * | 8/2006 | Trautman .............. A61B 17/205 604/22 |
| 7,250,037 | B2 | 7/2007 | Shermer et al. |
| 7,419,481 | B2 | 9/2008 | Trautman et al. |
| 7,798,987 | B2 | 9/2010 | Trautman et al. |
| 2002/0087182 | A1 | 7/2002 | Trautman et al. |
| 2002/0123675 | A1 | 9/2002 | Trautman et al. |
| 2003/0045837 | A1 | 3/2003 | Delmore et al. |
| 2003/0069548 | A1 | 4/2003 | Connelly |
| 2005/0096586 | A1 | 5/2005 | Trautman et al. |
| 2005/0228313 | A1 | 10/2005 | Kaler et al. |
| 2005/0261631 | A1 | 11/2005 | Clarke et al. |
| 2007/0073220 | A1 | 3/2007 | Bunce |
| 2007/0161964 | A1 | 7/2007 | Yuzhakov |
| 2008/0009811 | A1 | 1/2008 | Cantor |
| 2008/0051699 | A1 | 2/2008 | Choi et al. |
| 2008/0108958 | A1 | 5/2008 | Carter |
| 2008/0114298 | A1 | 5/2008 | Cantor et al. |
| 2008/0195035 | A1 | 8/2008 | Frederickson et al. |
| 2008/0208146 | A1 | 8/2008 | Brandwein et al. |
| 2009/0198189 | A1 * | 8/2009 | Simons .............. A61M 37/0015 604/173 |
| 2009/0254041 | A1 | 10/2009 | Krag et al. |
| 2010/0222743 | A1 | 9/2010 | Frederickson et al. |
| 2011/0172645 | A1 | 7/2011 | Moga et al. |

FOREIGN PATENT DOCUMENTS

| | | |
|---|---|---|
| WO | WO 1998/28037 | 7/1998 |
| WO | WO 2000/74766 | 12/2000 |
| WO | WO 02/32480 | 4/2002 |
| WO | WO 2006/055795 | 5/2006 |
| WO | WO 2007/002521 | 1/2007 |
| WO | WO 2007/002522 | 1/2007 |
| WO | WO 2007/002523 | 1/2007 |
| WO | WO 2007/005102 | 1/2007 |
| WO | WO 2007/124411 A1 | 11/2007 |
| WO | WO 2008/091602 | 7/2008 |
| WO | WO 2011/014514 | 2/2011 |
| WO | WO 2005/094526 | 7/2011 |
| WO | WO 2011/084951 | 7/2011 |
| WO | WO 2011/014240 | 11/2011 |

OTHER PUBLICATIONS

Brochure from MSS Software (2012) entitled "Barcode Solutions"; [retrieved from the internet on Mar. 19, 2014]; 2 pgs; available at http://www.mss-software.com/sofware.aspx?gclid=Clzbs9719KgCFRDPKgodc344Sg.

Brochure from Tech Target (2009-2014) entitled "SearchHealthIT.com"; [retrieved from the internet on Mar. 19, 2014] 23 pgs. available at http://searchhealthit.techtarget.com/.

Brochure from Stanley Black & Decker, Inc. (2011) entitled "CribMaster"; [retrieved from the internet on Mar. 19, 2014] 1 pg. available at http://www.cribmaster.com/vid-barcodeinventorytracking.html.

Brochure from JDA Software Group Inc. (2014) entitled "jda Focus Outperform"; [retrieved from the internet on Mar. 19, 2014] 3 pgs; available at http://www.jda.com/?mdi=24industries/healthcare.jsp.

* cited by examiner

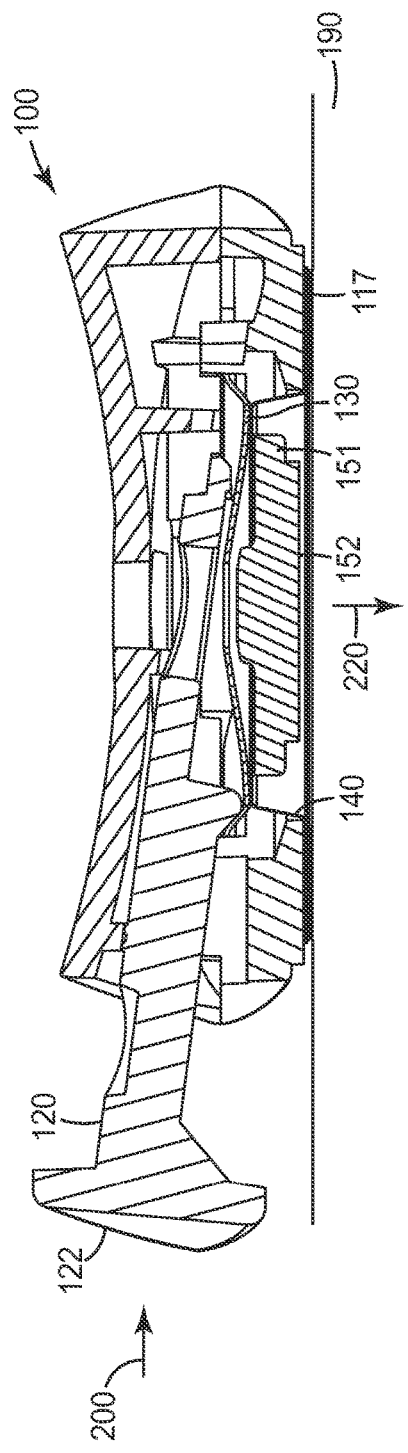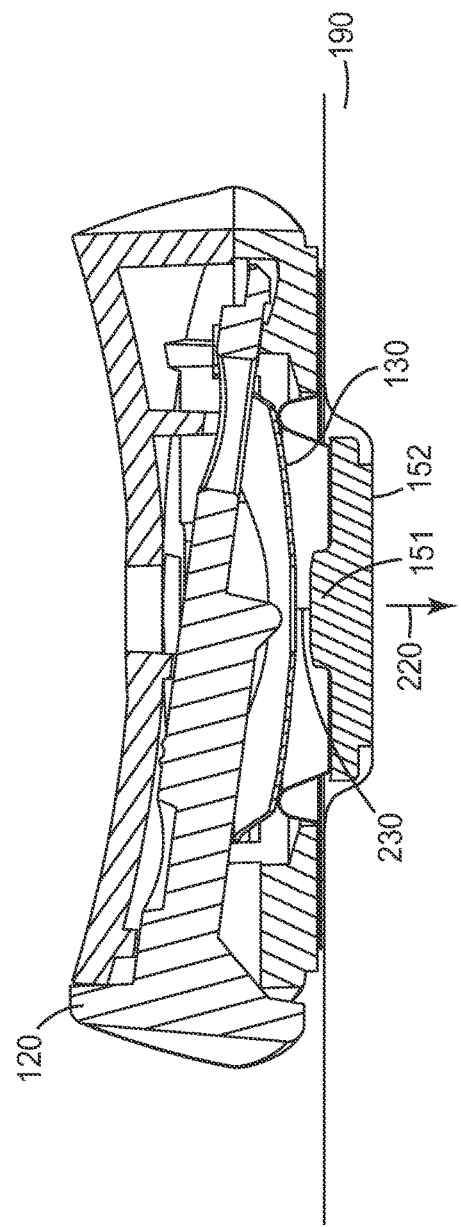
FIG. 5A
FIG. 5B

INTEGRATED MICRONEEDLE ARRAY DELIVERY SYSTEM

CROSS REFERENCE TO RELATED APPLICATIONS

This application is a national stage filing under 35 U.S.C. 371 of PCT/US2012/059273, filed Oct. 9, 2012 which claims priority to U.S. Provisional Patent Application No. 61/546,340, filed Oct. 12, 2011, the disclosure which is incorporated by reference in its entirety herein.

BACKGROUND

Only a limited number of molecules with demonstrated therapeutic value can be transported through the skin, even with the use of approved chemical enhancers. The main barrier to transport of molecules through the skin is the stratum corneum (the outermost layer of the skin).

Devices including arrays of relatively small structures, sometimes referred to as microneedles or micro-pins, have been disclosed for use in connection with the delivery of therapeutic agents and other substances through the skin and other surfaces. The devices are typically pressed against the skin in an effort to pierce the stratum corneum such that the therapeutic agents and other substances can pass through that layer and into the tissues below. Microneedles of these devices pierce the stratum corneum upon contact, making a plurality of microscopic slits which serve as passageways through which molecules of active components can be delivered into the body. In delivering an active component, the microneedle device can be provided with a reservoir for temporarily retaining an active component in liquid form prior to delivering the active component through the stratum corneum. In some constructions, the microneedles can be hollow to provide a liquid flow path directly from the reservoir and through the microneedles to enable delivery of the therapeutic substance through the skin. In alternate constructions, active component(s) may be coated on the microneedle array and delivered directly through the skin after the stratum corneum has been punctured.

Microneedle arrays can be used in conjunction with an applicator device capable of being used several times or single-use. The microneedle arrays are generally used once and then discarded.

Issues related to applying microneedles include the ability to effectively and consistently insert the needles to a desired depth in the skin, the ability to reliably hold the microneedles in proper contact with the skin during the period of administration, and the ability to apply consistent force for delivery.

SUMMARY

The present disclosure provides a low-profile system for delivering a microneedle array. The delivery system includes a housing that may be secured to and temporarily worn on a patient's skin. A carrier assembly coupled to a microneedle array is received in the housing proximate an applicator device. The applicator device can include an actuator and a stored energy device. While the carrier assembly is at least releasably secured to the housing, it is typically not attached or otherwise fixed to any portion of the applicator device. As such, the applicator device will not appreciably interfere with the travel of the carrier assembly after it transfers the force necessary to pierce the stratum corneum. Since the carrier assembly is not attached to the applicator device, it is free to continue moving forward with the motion of the skin even after the applicator device recoils or moves in a direction away from the skin. This independent motion may reduce the tendency for the microneedles to stop penetrating or to be pulled out of the skin. Increased and consistent depth of penetration can result in improved delivery across the stratum corneum.

In delivery system embodiments that include a stored energy device, the variability in force applied to the array may be reduced. In certain previous delivery systems, increasing the amount of energy transferred to the microneedle array meant an increase in the amount of applied energy by the user or the distance the microarray traveled before reaching the skin. A stored energy device is configured to store a certain amount of potential energy that can be released upon transfer of a predetermined amount of activation energy to a surface of the device. By placing a stored energy device between the user-applied force and the carrier assembly, the velocity at which the array impacts the skin may be more closely regulated. The above benefits can be realized in an applicator that is easy to handle, simple to use, low cost, and suitable for disposale or reuse.

The present disclosure provides an integrated system for delivering a microneedle array. In certain embodiments, the system includes a housing having a cavity therein and an applicator device coupled thereto. A carrier assembly coupled to solid microneedle array is received in the cavity. A portion of the carrier assembly is attached to the housing proximate the cavity and is in contact with a portion of the applicator. Neither the carrier nor the array is attached to the applicator device.

In certain embodiments, the carrier assembly further includes flexible membrane having a bellowed height sufficient to place the carrier assembly proximate a surface of the stored energy device. In certain embodiments, the applicator device includes a bifurcating spring.

The present disclosure also provides methods for delivering a microneedle array to the surface of the skin. In certain embodiments, the method includes providing a delivery system that includes a housing having a cavity therein and an applicator device coupled thereto; a carrier assembly coupled to solid microneedle array received in the cavity; a portion of the carrier assembly is attached to the housing proximate the cavity and is in contact with a portion of the applicator; and neither the carrier nor the array are attached to the applicator device. The method further includes placing the housing against the skin surface; and transferring an activation energy to the carrier via the applicator device, thereby driving the array and carrier towards the skin.

As used herein, "activation energy" refers to the minimum amount of energy required to release the potential energy stored within a stored energy device.

As used herein, "application energy" refers to the energy released upon activation of a stored energy device and applied to a microneedle carrier.

As used herein, "array" refers to the medical devices described herein that include one or more structures capable of piercing the stratum corneum to facilitate the transdermal delivery of therapeutic agents or the sampling of fluids through or to the skin. "Microstructure," "microneedle" or "microarray" refers to the specific microscopic structures associated with the array that are capable of piercing the stratum corneum to facilitate the transdermal delivery of therapeutic agents or the sampling of fluids through the skin.

As used herein, "carrier assembly" refers to at least a microneedle array and any structure used to couple the array to a housing. For example, the carrier assembly can refer to an array, a flexible membrane, and an adhesive layer. As another example, the carrier assembly refers to the array and an array carrier.

As used herein, "solid microneedle array" means an array comprised of microneedles of any size and shape that do not have an exposed bore therethough, in contrast to hollow microneedle arrays.

As used herein, "travel distance" refers to the distance traveled by an element of the delivery system upon actuation. For example, the travel distance for a stored energy device may be different than the travel distance for the array.

The terms "comprises" and variations thereof do not have a limiting meaning where these terms appear in the description and claims.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As recited herein, all numbers should be considered modified by the term "about".

As used herein, "a," "an," "the," "at least one," and "one or more" are used interchangeably. Thus, for example, a delivery apparatus comprising "a" stored energy device can be interpreted to comprise "one or more" stored energy devices.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exhaustive list.

BRIEF DESCRIPTION OF THE DRAWINGS

The invention will be further described with reference to the drawings, wherein corresponding reference characters indicate corresponding parts throughout the several views, and wherein:

FIGS. 5A-C are cross-sectional views of the delivery system of the previous figures in operation.

Figure 1:
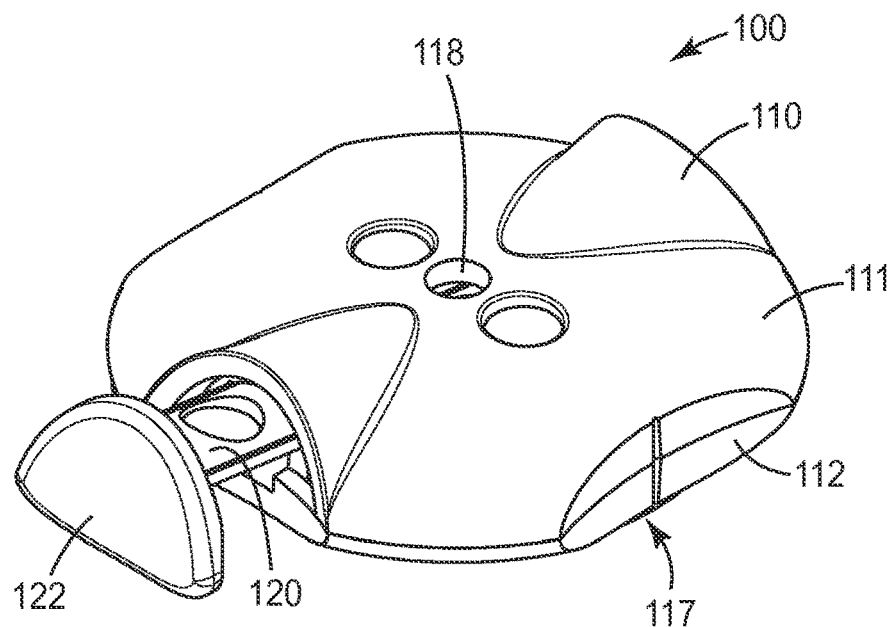
FIG. 1 is a perspective view of a microneedle delivery system according to one embodiment of the present disclosure.

While the above-identified figures set forth several embodiments of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention.

DETAILED DESCRIPTION OF ILLUSTRATIVE EMBODIMENTS

One embodiment of a delivery system is depicted in FIGS. 1-4. A delivery system 100 includes a device housing 110. The housing 110 can be self-contained and compactly constructed to provide a relatively low profile and small footprint for, among other factors, ease of use and patient comfort. In the embodiment illustrated FIGS. 1 and 2, the housing 110 may include lower housing portion 112 and mating upper housing portion 111. Alternatively (though not depicted), the delivery system may include a unitary housing. Upper and lower housing portions 111 and 112 may be secured together by any suitable means including, but not limited to, snap-fit together or coupled by pivots, frictional interference fits, welding, heat-staking, solvent bonding, mechanical fasteners, and the like. Housing 110 may be made of suitable lightweight materials compatible for ease of patient and practitioner handling The materials used in housing 110 may include, but are not limited to, plastics, metals, composite materials, and combinations thereof. For example, the housing 110 can be made of thermoplastics such as polypropylene, polybutylene terephthalate, polystyrene, polyethylene, polythermide, polyethylene terephthalate, polystyrene, polyvinyl chloride, polymethylmethacrylate, acrylonitrile-butadiene styrene, polycarbonate, and blends thereof. Other possible materials include metals, such as aluminum, steel, and stainless steel. Further, upper housing portion 111 may include a window 118 that allows a user to easily visually observe the operation of the elements within the cavity 116. Additionally or alternatively, the upper housing portion 111 can include transparent material to allow a user to visually inspect the application of a microneedle array.

The housing 110 includes a cavity 116 that receives a carrier assembly 150. The carrier assembly 150 includes an array carrier 151 and a microneedle array 152 coupled to a surface thereof. The microneedle array comprises a major plane that is oriented generally parallel to a skin surface 190 (as depicted in FIG. 5A) during use of the delivery system. Microneedle array 152 can include one or more needle or needle-like structures as well as other structures capable of piercing the stratum corneum. The microneedles are typically less than 900 microns, often less than 500 microns in height, and sometimes less than 300 microns in height. The microneedles are typically more than 20 microns in height, often more than 50 microns in height, and sometimes more than 125 microns in height. A stored energy device 130 is received proximate to or within the cavity 116 near a surface of the carrier assembly 150. The stored energy device can also be in direct contact with a portion of the carrier assembly 150. In other embodiments, the distance between the assembly 150 and the stored energy device 130 can vary, allowing the stored energy device to travel a certain distance before contacting the assembly 150.

The microneedles useful in the various embodiments of the invention may comprise any of a variety of configurations, including but not limited to those described in the following patents and patent applications. One embodiment for the microneedles comprises the structures disclosed in United States Patent Application Publication No. US2003/0045837. The disclosed microstructures in the aforementioned patent application are in the form of microneedles having tapered structures that include at least one channel formed in the outside surface of each microneedle. The microneedles may have bases that are elongated in one direction. The channels in microneedles with elongated bases may extend from one of the ends of the elongated bases towards the tips of the microneedles. The channels formed along the sides of the microneedles may optionally be terminated short of the tips of the microneedles. The microneedle arrays may also include conduit structures formed on the surface of the substrate on which the microneedle array is located. The channels in the microneedles may be in fluid communication with the conduit structures. Another embodiment for the microneedle devices comprises the structures disclosed in co-pending United States Patent Application Publication No. US2005/0261631 which describes microneedles having a truncated tapered shape and a controlled aspect ratio. Still another embodiment for the microneedles comprises the structures disclosed in U.S. Pat. No. 6,091,975 (Daddona, et al.) which describes blade-like microprotrusions for piercing the skin. Still another embodiment for the microneedles comprises the structures disclosed in U.S. Pat. No. 6,312,612 (Sherman, et al.) which describes tapered structures having a hollow central channel. Still another embodiment for the micro arrays comprises the structures disclosed in International Publication No. WO00/74766 (Garstein, et al.) which describes hollow microneedles having at least one longitudinal blade at the top surface of tip of the microneedle.

The cavity 116 can be defined by cooperation of both the upper housing 111 and the lower housing 112, or may be solely contained in the lower housing 112. The minimum height of the cavity 116 is at least partially determined by the desired travel distance of the microneedle array 152 before reaching the skin surface and the travel distance of the stored energy device. Accordingly, the height of cavity 116 in some embodiments may be no greater than 2 centimeters. In other embodiments, the height of the cavity 116 may be no greater than 1 centimeter, in other embodiments no greater than 8 millimeters, in yet other embodiments no greater than 5 millimeters. In certain embodiments, the height of the cavity is at least 1 millimeter, in other embodiments at least 2 millimeters, in other embodiments at least 5 millimeters. Cavities less than 1 millimeter in height may not allow sufficient travel distance for the array to pierce the stratum corneum and/or may require application of greater force to the array than safe or desirable in a low-profile device.

Lower housing portion 112 includes a base 114, which can be generally planar, and defines an opening 115 to the cavity 116. The base 114 includes an attachment surface 117, which at least partially envelopes the opening 115 and can also be generally planar. The attachment surface 117 can include an adhesive layer 160 for eventual attachment of the housing 110 to a patient's skin surface. Adhesive layer 160 can be a continuous coating, a patterned coating, or discrete portions of adhesive, or combinations thereof. In certain embodiments, a first major surface of the adhesive can be coupled to a release liner 170 (see FIG. 3) prior to use.

It may be desired that the height of the housing be designed for ease of handling and operation. Accordingly, the height of the housing 110 may be no greater than 3 centimeters. In other embodiments, the height of the housing may be no greater than 1 centimeter, in other embodiments no greater than 5 millimeters, in other embodiments no greater than 3 millimeters. In certain embodiments, the height of the housing is at least 1.5 millimeters, in other embodiments at least 2 millimeters, in other embodiments at least 5 millimeters. Housings less than 1.5 millimeters in height may not allow sufficient travel distance for the array to pierce the stratum corneum and may be too difficult to handle. On the other end of the spectrum, housings greater than 3 centimeters in height can be unwieldy and difficult to maintain adherence to skin.

Figure 2:
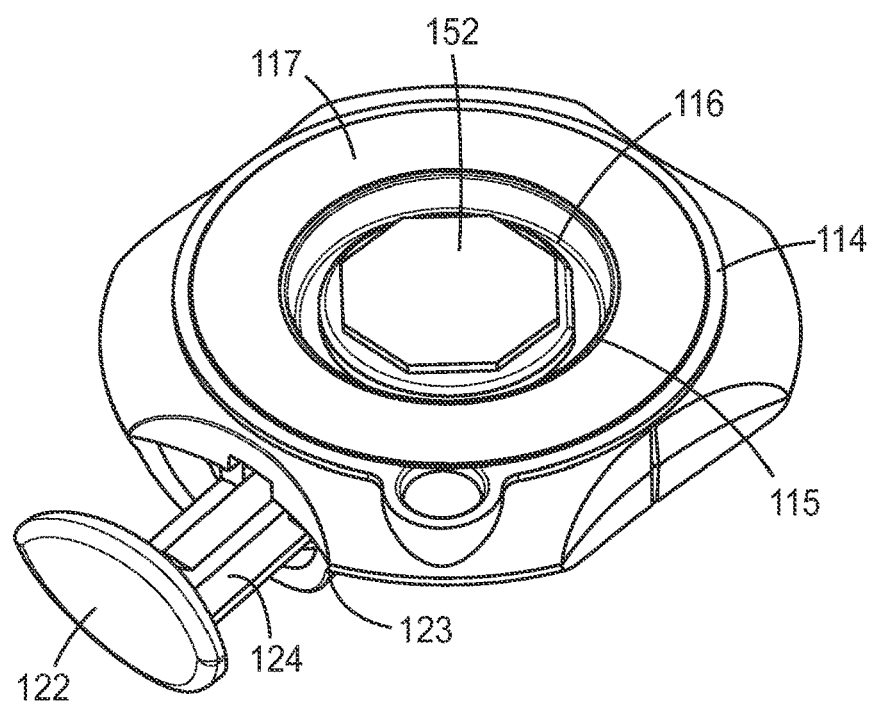
FIG. 2 is a perspective view of the microneedle delivery system of FIG. 1.
Figure 3:
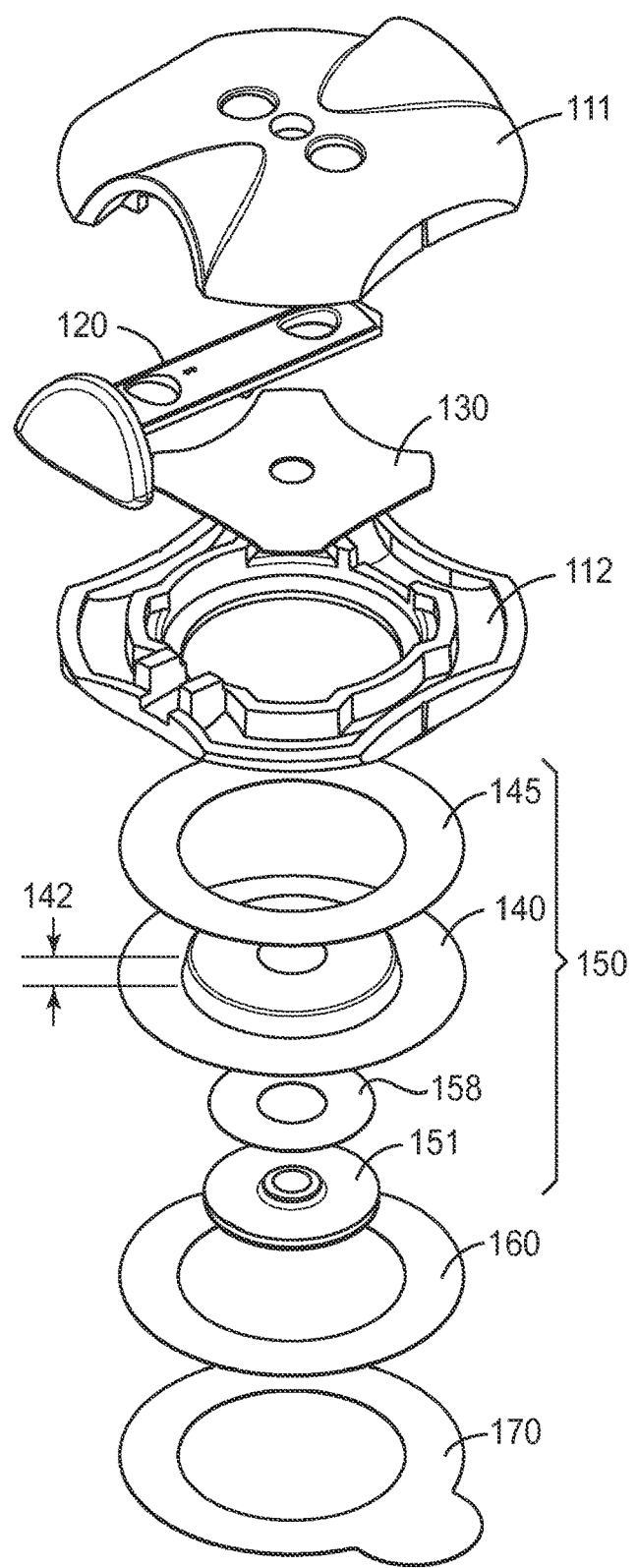
FIG. 3 is an exploded view of the microneedle delivery system of FIG. 1.

Referring now to FIGS. 2 and 3, additional aspects of the delivery system 100 are further detailed. In certain embodiments, the stored energy device 130 can be secured to the interior of the housing by any suitable attachment means, including but not limited to adhesives, fasteners, interference-fits, and the like. In certain embodiments, peripheral portions of the stored energy device 130 may be contained between the upper housing 111 and lower housing 112, and rested on a groove or ridge portion proximate the cavity 116 without any additional attachment. The stored energy device 130 is actuatable to apply force in a direction generally orthogonal to the attachment surface 117 and major plane of the array 152. Suitable stored energy devices include, but are not limited to, domed springs, deflected beams, coiled springs, leaf-like springs, propellant canisters, and the like. In most embodiments, a portion of the stored energy device can travel unimpeded within the housing and/or cavity to deliver the application force to the carrier assembly 150.

The stored energy device 130 is actuatable for applying force (i.e., application energy) to carrier assembly 150, thereby accelerating at least a portion of the assembly to a velocity before impact sufficient to pierce the skin. It is desirable that a consistent, predetermined amount of force is necessary to actuate the stored energy device, thereby resulting in a consistent amount of force applied normal to the skin during actuation. The microneedle array 152 typically reaches a velocity before impact ranging from between about 2 and about 20 m/sec before the microneedle array impacts a patient's skin. More typically, the array strikes a patient's skin at a velocity before impact ranging from between about 4 and about 15 m/sec. In certain preferred embodiments, the velocity at impact is consistently over 10 m/sec. It can also be desirable, however, to limit the velocity to prevent or reduce the stimulation of underlying nerve tissue on or after impact.

Figure 6:
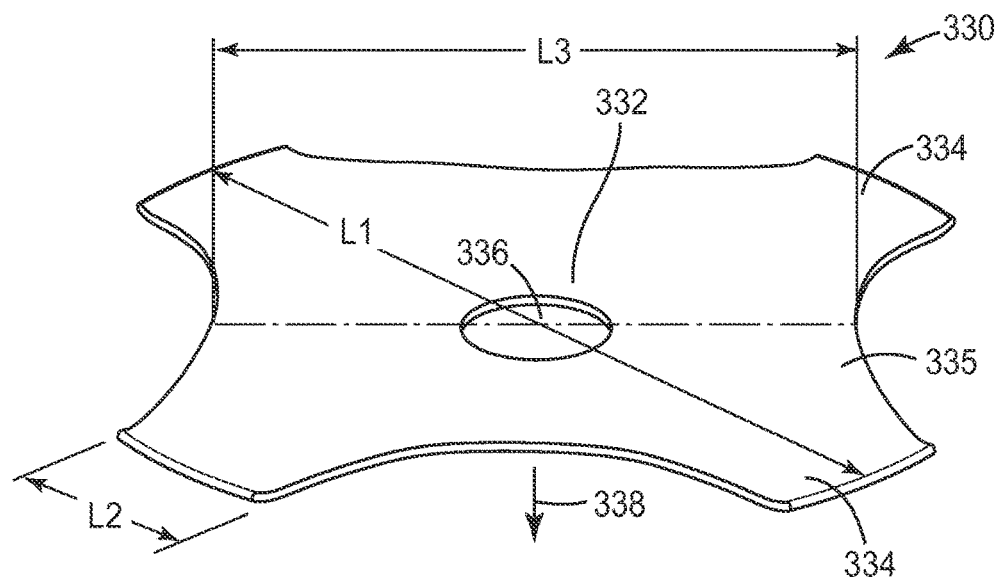
FIG. 6 is a perspective view of a bifurcating spring according to certain embodiments of the disclosure.
Figure 7:
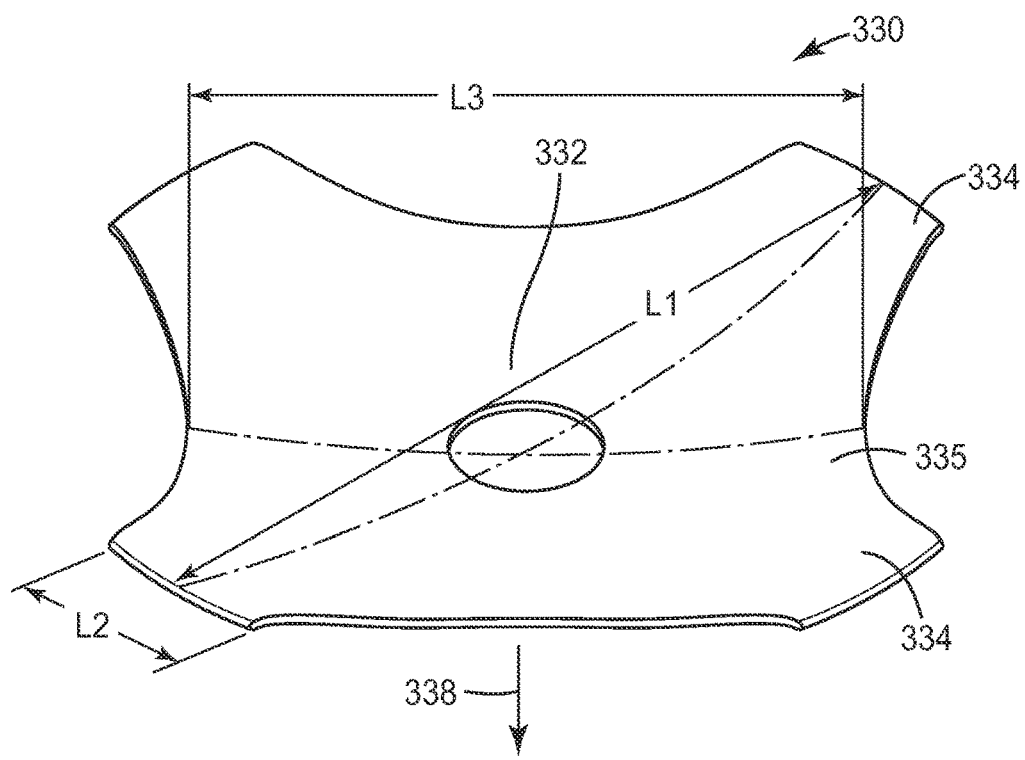
FIG. 7 is a perspective view of a bifurcating spring according to another aspect of the disclosure.
Figure 9:
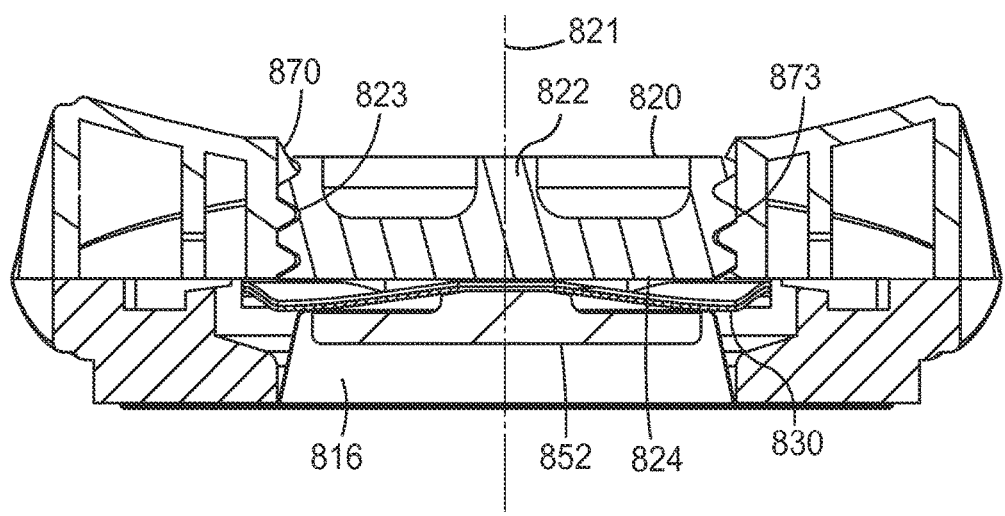
FIG. 9 is a cross-sectional view of the delivery system of FIG. 8.
Figure 11:
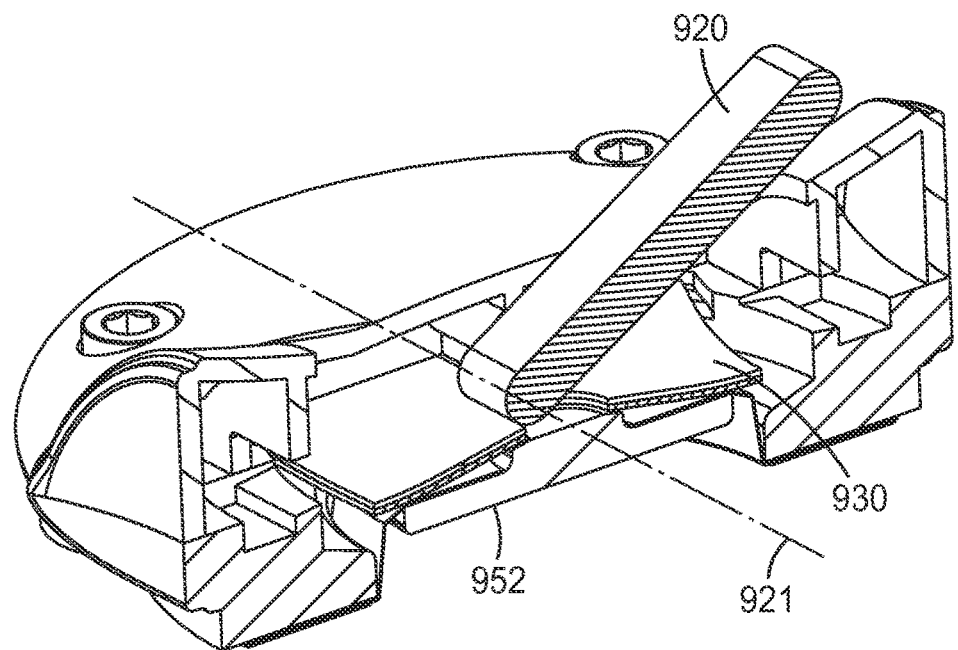
FIG. 11 is a cross-sectional view of the delivery system of FIG. 10.

In certain embodiments, the stored energy device 130 is configured so that it will undergo a bifurcated (i.e., stepwise) motion in a direction generally orthogonal to the attachment surface and/or the major plane of a microneedle array. For example, the stored energy device in such embodiments can be a domed, bifurcating spring as depicted in FIGS. 6 and 7. The stored energy device can also include a plurality of bifurcating springs, as depicted in FIGS. 9 and 11. As used herein, a bifurcating spring is a spring that undergoes a shape change as a result of a predetermined force applied normal to a major plane of the spring. Using methods further described herein, it is possible to manufacture bifurcating springs that can store a greater or substantially greater amount of energy than can be comfortably applied to the delivery system by a user during use.

One embodiment of such a bifurcating spring is depicted in a loaded, stable configuration (i.e., a state prior to exterior application of energy) in FIG. 6. In addition to the depicted springs, other suitable springs include Belleville washers and domed springs. The undulating spring 330 includes a generally circular central portion and one or more legs 334. In certain embodiments, the spring 330 can include an aperture 336 proximate the center. The loaded spring 330 is designed to store a certain amount of potential energy. This potential energy is converted to a kinetic energy once a predetermined amount of activation energy is transferred to the first major surface 332 of the spring 330. This results in the spring bifurcating and reaching the destabilized configuration as depicted in FIG. 7. The release of kinetic energy occurs in a direction 338 generally orthogonal to the major plane of the spring, which results in the center of the spring traveling a certain distance between stable and destabilized states.

Due to the potential energy stored within, the bifurcating spring 330 may release energy greater than the energy necessary to cause bifurcation (i.e., the activation energy). In certain embodiments, the kinetic energy (i.e., application energy when transferred to a microneedle array or carrier assembly) is at least twice the activation energy. In certain embodiments, the application energy is 4 times greater than the activation energy, in other embodiments, at least 10 times, and in yet other embodiments at least 20 times greater than the activation energy. As the bifurcating spring is potentially capable of releasing substantially more energy the amount of normal force applied to the skin can be minimized while generating sufficient application velocity and the user to user variability in force applied to the carrier assembly is reduced. This reduced variability can result in more consistent and repeatable microneedle penetration.

A bifurcating spring according to the present disclosure may be created by, e.g., applying a predetermined force (i.e., load) to the center of an otherwise non-bifurcating domed spring, while supporting the periphery. Suitable non-bifurcating springs include but are not limited to stainless steel domed springs available from Snaptron Inc., Windsor, Colo. The force applied to a spring surface is preferably sufficient to cause plastic deformation of at least a portion of the spring. In certain embodiments, a press or probe applies a displacement to a surface 332 of the spring at a constant rate. The press continues past the point of bifurcation and until the desired force has been applied after bifurcation. At this point, the probe stops moving and remains in place for a given amount of hold time. In the case of a "zero" hold time, the press begins to retract immediately after reaching the desired bend force. Without wishing to be bound by theory, both the load applied after bifurcation and the time over which the load is applied appear to be positively correlated with the energy necessary to activate the spring, and to a lesser degree, the potential energy released on bifurcation. After a certain time, however, an increase in hold time may not amount to an appreciable increase in stored energy. The energy applied after activation of the spring is further influenced by, inter alia, the material of the spring, the thickness of the material, and the geometry of the dome. By manipulating at least these variables, both the energy required to activate the bifurcating spring and the energy applied to a carrier assembly can be tailored to suit the needs of a desired microneedle delivery system.

The housing 110 further includes an actuator 120. The actuator 120 cooperates with the stored energy device 130 to form an applicator device. The actuator 120 includes a finger engageable portion 122 that is adapted to cover actuator opening 123 formed in the upper housing portion 111. In the embodiment depicted in FIGS. 1-5, the actuator further includes an extended arm portion 124 that extends from finger engageable portion 122 through opening 123 and into the cavity 116. The arm portion 124 can include a wedge 126 or other protrusion. The actuator 120 is movable within the housing at an angle relative to the attachment surface 117. Movement of the wedge 126 relative to the stored energy device 130 applies a force in a direction generally orthogonal to the major plane of the array 152.

In other embodiments, the actuator may not actually contact the stored energy device 130, but can remove an impediment to the release of kinetic energy. For example, the actuator may engage and deform a releasable retaining device that holds the stored energy device in a primed position. Deformation or displacement of the releasable retaining device may then allow the stored energy device to discharge the potential energy stored therein.

Figure 4:
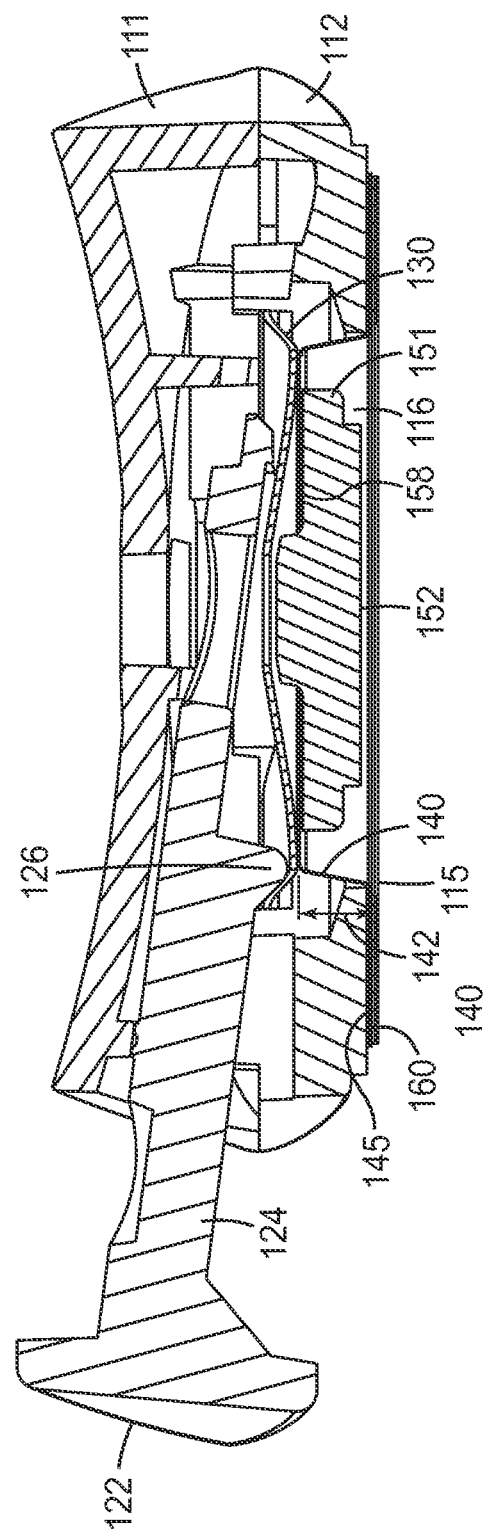
FIG. 4 is a cross-sectional view of the microneedle delivery system of FIG. 1.

As depicted in FIGS. 3 and 4, carrier assembly 150 includes a solid microneedle array 152, an array carrier 151, and a flexible membrane 140. The microneedle array 152 can be attached to a first surface of array carrier 151 by any suitable attachment means. As shown in FIG. 3, the attachment means is an adhesive 157, which may be in the form of a continuous coating, a patterned coating, or discrete portions of adhesive. In one aspect, the adhesive attachment is non-permanent, that is, after application of the microneedle array, the carrier may be removed from the skin surface though all or part of the array remains. Other suitable attachment means for connecting the microneedle device 152 and the array carrier 151 include snap-fit connections, hook and loop (e.g., Velcro™) attachments, magnetic attachment, heat bonding, welding, or any other suitable conventional attachment method known to one of ordinary skill in the art. In other embodiments, the microneedle array may be formed or molded as an integral portion of the array carrier 151.

The microneedle array 152 depicted in FIG. 2 has a hexagonal shape, but any of a number of shapes and sizes are suitable for use with application devices of the present invention.

At least a portion oft the array carrier 151 can be formed so as to be relatively rigid. Suitable materials include polymers, such as liquid crystal polymers, polypropylene, polybutylene terephthalate, polystyrene, polyethylene, polythermide, polyethylene terephthalate, polystyrene, polyvinyl chloride, polymethylmethacrylate, acrylonitrile-butadiene styrene, polycarbonate, and blends thereof. The rigidity can provide support for the microneedle array and may assist in the transfer of application energy. Other materials are also contemplated, including metals, ceramics, and other materials that will be apparent to those skilled in the art. In certain embodiments, the array carrier can be comprised of the same material as the microneedles of the microneedle array.

The carrier assembly 150 can include a flexible membrane 140 coupled to a surface of the array carrier 151 opposite the microneedle array 152 via attachment mechanism 158. The flexible membrane 140 includes a chamber having a bellowed height 142. The bellowed height 142 is preferably such that the carrier assembly 150 is retained in contact with or in close proximity to a portion of the stored energy device 130 when received in the cavity 116. The flexible membrane 140 is preferably capable of retaining the bellowed height 142 prior to the application of force to the carrier assembly 150 via the stored energy device. For example, the membrane can be constructed of CoTran 9701 polyurethane film, available from 3M Company, St. Paul, Minn. Other polymeric films capable of maintaining the bellowed height are also suitable for use as a membrane. In certain embodiments, the flexible membrane includes a material that is sterilizable and/or maintains a sterile barrier.

The flexible membrane 140 can be vented or non-vented. When the delivery system 100 is placed on the skin surface, a chamber of air may be formed between the skin surface, the adhesive 160, the membrane/array assembly, and potentially a portion of the lower housing 112. As used herein, a membrane is "vented" when it includes deliberate apertures or channels to allow the flow of fluid out of the chamber. In certain preferred embodiments, at least a portion of the membrane is non-vented, in that is does not include any deliberate means for fluid to flow out of the chamber. Non-vented membranes may surprisingly provide better depth of microneedle penetration in the skin, as well as more consistent penetration levels across the entire array. Furthermore, a non-vented membrane may allow for a carrier assembly to be provided pre-sterilized and pre-loaded with the agent intended for transdermal delivery.

The carrier assembly 150 may be secured within the cavity 116 via attachment of the flexible membrane 140. For example, a certain length of the flexible membrane 140 can be secured via attachment mechanism 145 to portions of the lower housing 112 proximate the opening 115. Additionally or alternatively, the chamber can be sized to create an interference fit with cavity 116, such that the carrier assembly 150 may simply be pressed into the housing.

The carrier assembly 150, or a portion thereof, can also be coupled or releasably coupled to the stored energy device 130. For example, the stored energy device 130 may include one or more apertures and array carrier 151 can include one or more elongated protrusions capable of being received in the apertures. Once so received, the protrusion may be riveted to the stored energy device 130. In other embodiments, the carrier assembly 150 may be secured to the stored energy device 130 via adhesive or other attachment means described herein.

In embodiments wherein the carrier assembly is attached or releasably attached to a stored energy device comprising a spring, the motion of the microneedle array is coupled to that of the spring. After activation and transfer of application energy (i.e., the release of the stored potential energy in the spring and its subsequent contact with the carrier assembly), both the spring and carrier assembly will move cooperatively towards the skin surface in the direction of the applied force. Impact of the assembly at the skin surface will also cause the skin to move in the direction of the applied force. At some point after activation, the spring reaches a point of maximum extension and will begin to travel away from the skin (i.e., recoil). The surface of the skin, however, may continue to move in the direction of the applied force. Since they are coupled to motion of the spring, the microneedles may stop penetrating or even pull out of the skin, leading to less and/or more inconsistent depth of penetration.

In one exemplary embodiment of the present disclosure, the stored energy device 130 is not attached or otherwise fixed to the carrier assembly 150. As such, following impact at the skin, the stored energy device 130 may freely recoil upwardly and vibrate without otherwise affecting the travel of the carrier assembly/microneedle array. Since the carrier assembly 150 is not attached to the stored energy device 130 after activation, it is free to continue moving forward with the motion of the skin; without regard to the recoil of the stored energy device 130. This independent motion may reduce the tendency for the microneedles to stop penetrating or to be pulled out of the skin. Increased depth and more consistent penetration of the microneedles can result in improved delivery across the stratum corneum.

The carrier assembly 150 can also be coupled to the housing 110 or cavity 116 without use of a flexible membrane 140 and without attachment to the stored energy device 130. For example, the array carrier can include protrusions that rest on an internal ridge or groove, providing an inference fit that allows for release of the carrier assembly upon application of minimal force. In addition to the exemplary embodiments described herein, one skilled in the art will appreciate additional means for temporarily securing the carrier assembly within the housing without coupling to the stored energy device 130.

The delivery system 100 may be provided to a practitioner or user fully assembled and/or coated with the agent to be delivered to the skin. In other embodiments, the carrier assembly is provided separately from the housing. In certain preferred embodiments, the stored energy device is provided in the loaded configuration, though it is also possible for the stored energy device to be primed after receipt or shortly before use.

Figure 5C:
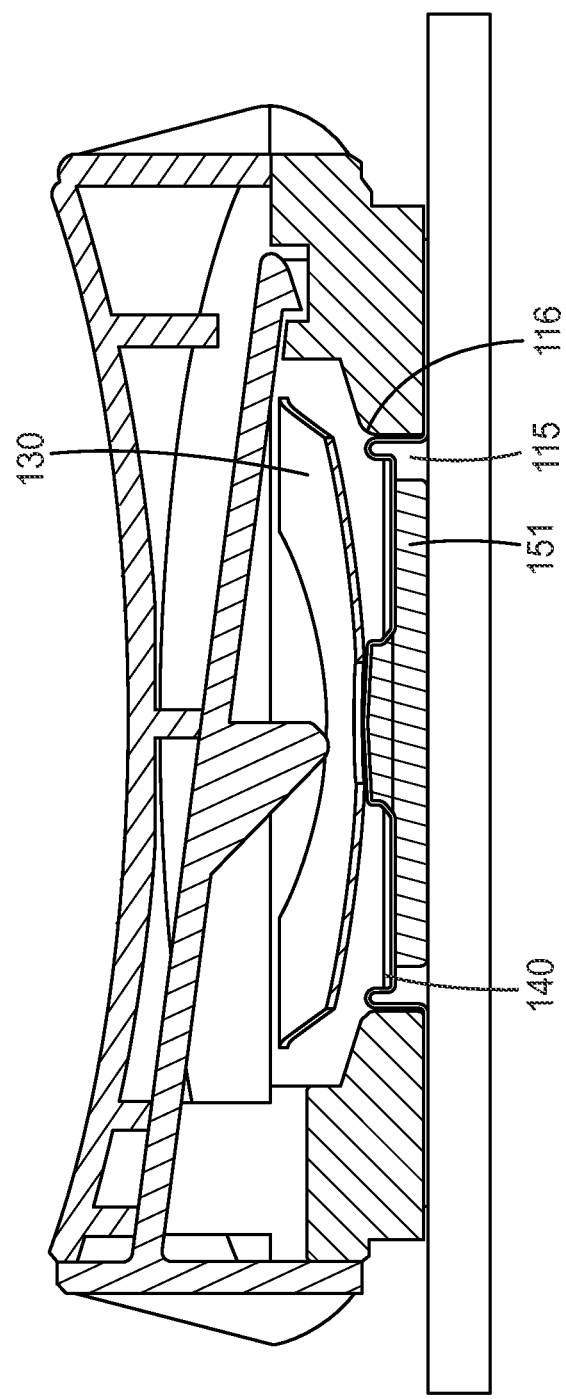

The present disclosure further provides for methods of delivering a microneedle array to a patient's skin surface. One method of delivering a microneedle array using decoupled delivery system 100 is depicted in FIGS. 5A-5C. Turning initially to FIG. 5A, the attachment surface 117 is placed proximate a patient's skin surface 190. Once placed and optionally secured via adhesive layer, a force may be applied to finger engageable portion 122 of the actuator 120. This force is typically applied in a direction 200 that is generally parallel to major plane of array and the attachment surface 117. The applied force moves the wedge 126 relative to the stored energy device, resulting in the application of force orthogonal to the major plane of the stored energy device 130. This application of force causes a transfer of energy (i.e., activation energy) to the stored energy device 130. When the activation energy exceeds a predetermined threshold, the stored energy device releases its potential energy, accelerating a portion of the device 130 towards the carrier assembly 150. In certain embodiments, the force required to release the potential energy is the stored energy device is no greater than 15 N, in some embodiments no greater than 8 N, and in some embodiments no greater than 5 N, and in yet other embodiments no greater than 1 N. In certain circumstances, it may be preferred that the force required be at least 2 N and no greater than 5 N. While it may be advantageous to reduce or minimize activation force, it will be appreciated by those skilled in the art that the activation force should be high enough to avoid inadvertent firing of the stored energy device before the user is ready to use the delivery system.

In releasing its potential energy, at least a portion of the stored energy device 130 travels in the direction of the skin surface. The stored energy device 130 will contact the carrier assembly 150, applying a force in a direction 220 generally orthogonal to the major plane of the microneedle array 152. In certain embodiments, the energy applied by the stored energy device is no greater than 0.3 J, in some embodiments no greater than 0.2 J, and in some embodiments no greater than 0.15 J, and in yet other embodiments no greater than 0.1 J. In certain embodiments, the energy applied by the stored energy device is at least 0.006 J, in some embodiments at least 0.01 J, and in some embodiments at least 0.05 J. In certain circumstances, it may be preferred that the force applied be at least 0.013 J and no greater than 0.12 J. This transfer of the application energy accelerates the carrier assembly 150 including the membrane 140 in the direction of the skin, with the assembly eventually emerging through opening 115. In certain embodiments, the application energy is at least twice the activation energy, in other circumstances at least 5 times the activation energy, in other embodiments at least 10 times the activation energy, in yet other embodiments at least 20 times the activation energy, and in yet other embodiments at least 30 times the activation energy.

FIG. 5B depicts the delivery system 100 at a time after the microneedle array 152 has impacted the skin. After transfer of application energy, the motion of the stored energy device 130 slows relative to the motion of the carrier assembly 150 and a measureable gap 230 may form between them. Depending on the physical characteristics of the stored energy device, carrier assembly, and skin, this gap may form and close one or more times before the stored energy device, carrier, and skin come to rest. After impact, the microarray, skin, and membrane continue to move in the direction 220 of the application force. Since the motion is decoupled, however, the carrier assembly 150 is free to move with the skin until the skin's point of maximum extension.

In certain embodiments, the membrane is capable of traveling a greater distance than the carrier assembly would travel due to the energy applied by the stored energy device 130. The length of membrane 140 received in the cavity 116, and the resultant bellowed height 142, can be accordingly designed to allow the membrane 140 to extend substantially beyond the attachment surface 117 of the housing 110.

Eventually, the skin and carrier assembly 150 will begin to recoil and dampen. As depicted in FIG. 5C, the carrier assembly may come to rest within the cavity 116, with substantially no portion thereof, with the exception of the microneedles, emerging from opening 115. In the depicted embodiment, the membrane 140 does not return to its original bellowed height 142, leaving room in the cavity 116 for the "fired" stored energy device and allowing the microneedles to remain at the desired penetration depth. In other embodiments, at least a portion of the array carrier 151 can emerge from the housing.

Since the user provides a force 200 which is in a direction essentially parallel to the surface of the skin, delivery system 100 can be activated without creating a significant skin dome and without substantially stretching the skin or otherwise disturbing the surface. In certain preferred embodiments, the delivery system does not create a skin dome or stretch the skin. While a small activation force in a direction orthogonal to the skin may be necessary to activate the stored energy device, the forces generated normal to the skin surface are essentially reacted against one another within the housing 110. Accordingly, the force actually applied to the skin in a direction normal to the plane of the skin is zero or near zero. In addition, the forces generated in a direction parallel to the plane of the skin in this embodiment are at least substantially transferred to the stored energy device as the wedge 126 slides across a surface thereof. Thus, the efficacy of the parallel sliding motion of the actuator will likely discourage the user from pushing the device in a direction normal to the skin during activation, further increasing the consistency of application.

Furthermore, the use of an actuator movable in direction generally parallel to the attachment surface with a high mechanical advantage may allow the activation force of the stored energy device to be set at a higher level, while maintaining a relatively low force required to be applied by the user. This may be particularly useful, as high activation forces can limit the patient population that can operate a particular delivery system. The parallel motion of the actuator may further reduce the variability in velocity of the array at impact.

FIGS. 8-11 depict additional implementations of a delivery system according to the present disclosure, particularly those featuring alternative actuators. Except as set out in the paragraphs that follow, the delivery systems 800 and 900 are substantially the same as the apparatus 100 described above and consequently a description of the similar aspects need not be repeated.

Figure 8:
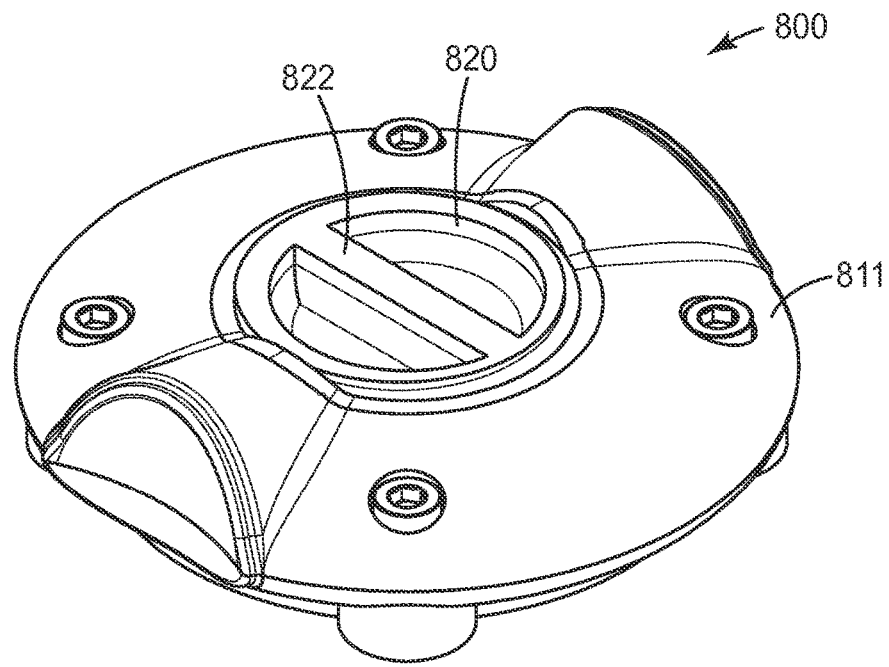
FIG. 8 is a perspective view of a microneedle delivery system according to another aspect of the disclosure.

As depicted in FIGS. 8 and 9, the delivery system 800 features a rotatable actuator 820 positioned above a stored energy device 830. The rotatable actuator 820 rotates about an axis of rotation 821 that is generally perpendicular to the major plane of the array 852. In other embodiments not depicted herein, the actuator 820 is configured to rotate about an axis angularly offset from axis 821. The rotatable actuator 820 includes helical threads 823 and a graspable ridge 822 on an exterior surface thereof. The upper housing 811 includes an aperture 870 located above the cavity 816 and stored energy device 830. The aperture 870 has one or more side wall portions including helical grooves 873 that correspond to the helical threads on the actuator 820. The rotation of the actuator 820 about the axis 821 brings an engagement surface 824 closer to the stored energy device 830. The actuator 820 may thus be rotated by a user until the engagement surface 824 contacts the stored energy device 830, eventually resulting in application of the predetermined activation force orthogonal to the major plane of the stored energy device 830 without substantial normal force applied to the skin.

Figure 10:
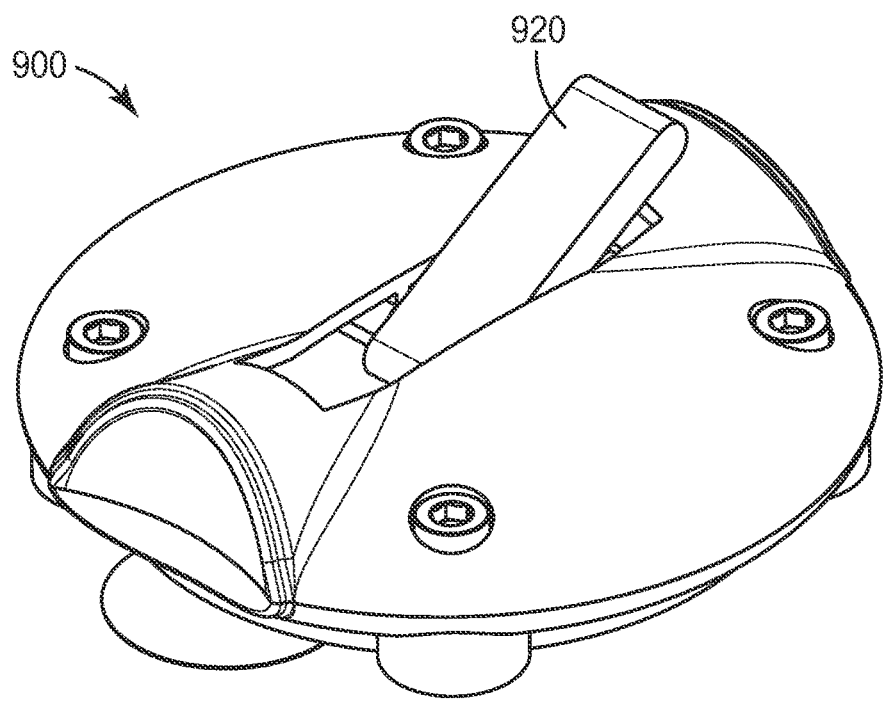
FIG. 10 is a perspective view of a microneedle delivery system according to another aspect of the disclosure.

FIGS. 10 and 11 depict a microneedle delivery system 900 featuring a different rotatable actuator. Actuator 920 comprises a cam rotatable about an axis 921. Rotation of the actuator 920 transfers a force orthogonal to the major plane of the stored energy device 930 and/or the microneedle array 952. The delivery systems 800 and 900 may also provide the potential benefits as described above, since equal and opposite forces react within the device leading to no or essentially no force being applied normal to the skin during activation.

Figure 12:
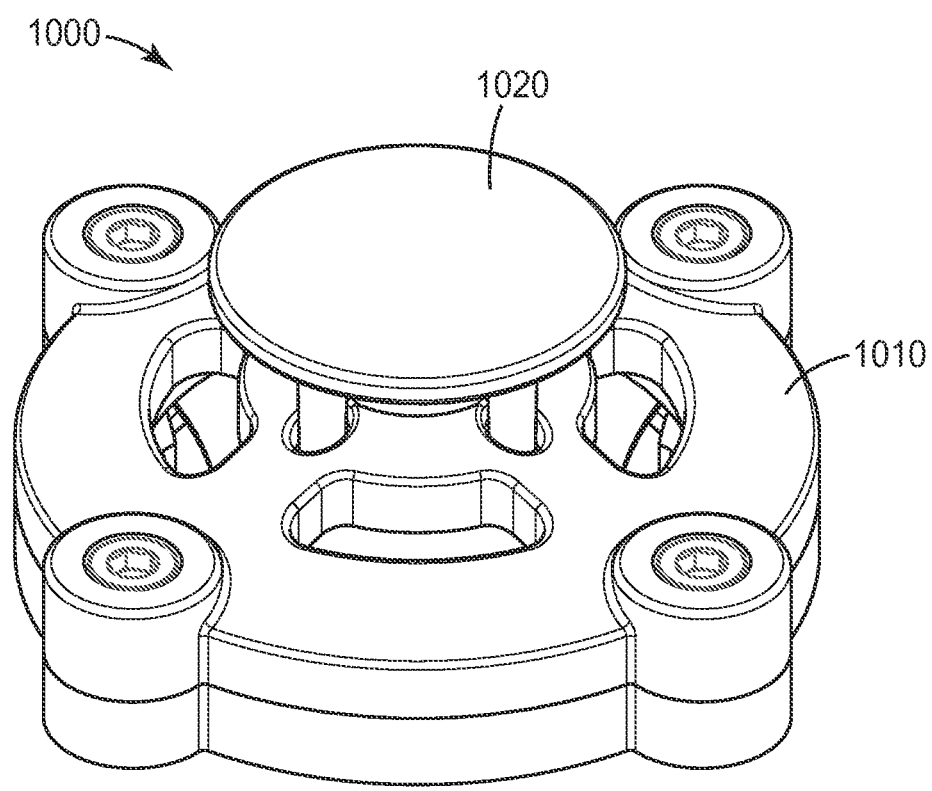
FIG. 12 is a perspective view of a perspective view of a microneedle delivery system according to yet another aspect of the disclosure.
Figure 13:
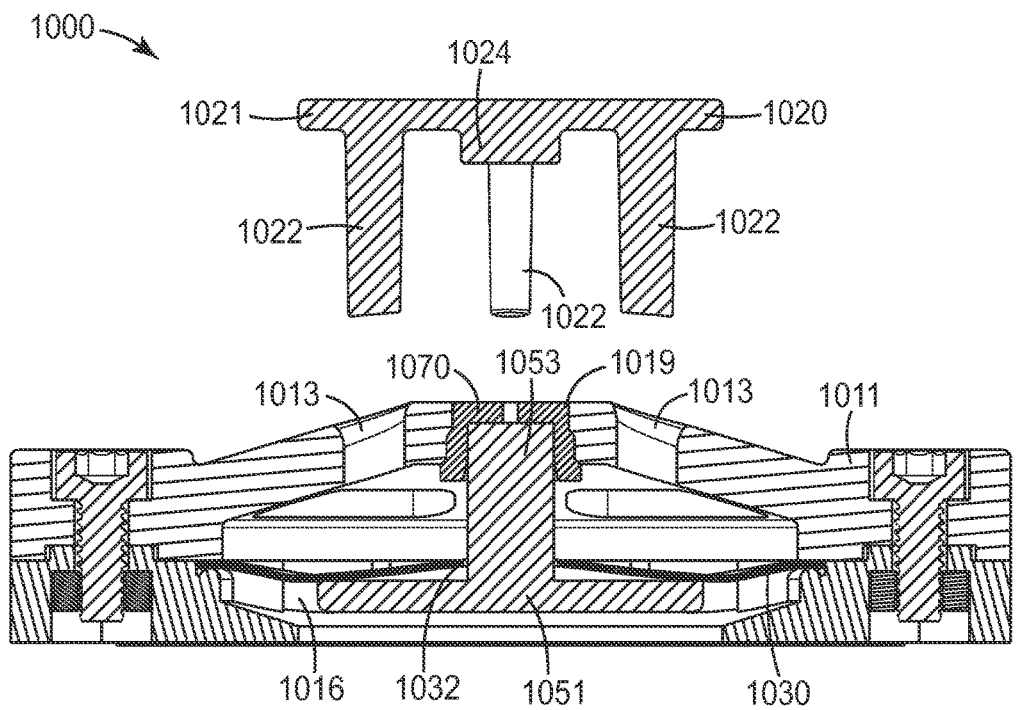
FIG. 13 is a cross-sectional view of the delivery system of FIG. 12.
Figure 14:
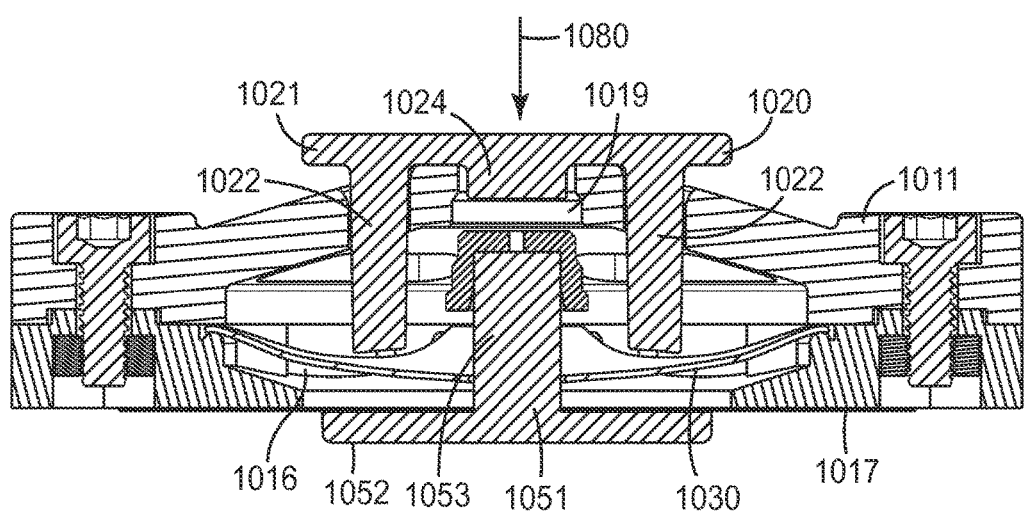
FIG. 14 depicts the delivery system of FIG. 12 in operation.

An alternative embodiment of a delivery system is depicted in FIGS. 12-14. Like the delivery systems discussed above, the delivery system 1000 includes a housing 1010 having a cavity 1016 defined therein; a stored energy device 1030 received in or proximate to the cavity; and a carrier assembly including a microneedle array 1052 coupled to an array carrier 1051. An upper housing portion 1011 includes an attachment cap 1070 received in a central aperture 1019. The attachment cap 1070 can be secured to the upper housing via releasable or other adhesive, interference fit, or other means known to those having skill in the art. Suitable materials for the attachment cap include thermoplastic elastomers, silicones, rubber, and other materials known to one skilled in the art.

The attachment cap 1070 receives the distal end of an elongated arm portion 1053 of the array carrier 1051. In certain embodiments, the end of the elongated arm portion is press fit into aperture 1019 without an attachment cap 1070. The arm portion 1053 also extends through an aperture in the center of stored energy device 1030. In certain embodiments, the arm portion 1053 is designed so that it may be press fit into the attachment cap 1070, while not engaging the periphery of the stored energy device aperture 1032 (i.e., the dimension of the aperture are greater than those of the distal end of the arm portion 1053). In other embodiments, the proximal end of the arm portion 1053 may be configured for an interference fit with the aperture 1032, obviating the need for the attachment cap. In yet other embodiments, the attachment cap and an interference fit between carrier and stored energy device can be used.

An actuator 1020 includes one or more posts 1022 extending from a generally planar base 1021. The posts 1022 extend through apertures 1013 in the upper housing into the cavity 1016 proximate to or in contact with the stored energy device 1030. The base 1021 also includes a center pedestal 1024 designed to engage attachment cap 1070 and/or arm portion 1053. The actuator 1020 may be provided already received housing 1010 or as a separate component.

One potential method of using the delivery system 1000 is depicted in FIG. 14. A user places actuator 1020 within the apertures in upper housing 1011. A force in a direction 1080 normal to the base 1021 and the attachment surface 1017 is then applied. When force is applied to the base 1021, the center pedestal 1024 pushes the attachment cap 1070 down to a point where it releases from the upper housing 1011 and is free to move independently of the housing 1010. The posts 1022 then engage the stored energy device 1030, transferring the activation energy thereto. The length of the posts 1022 can be designed so that the attachment cap 1070 (or arm portion 1053) is released first, followed by transfer of energy to the stored energy device 1030. In other embodiments, the attachment cap 1070 or arm portion 1053 is released and the stored energy device 1030 is activated at essentially the same time. In yet other embodiments, the application energy transferred to the carrier assembly is sufficient to dislodge the arm portion 1053 from the attachment cap 1070 or the attachment cap 1070 from the housing. Alternatively, portions of the attachment cap 1070 can expand upon application of pressure via the pedestal 1024, releasing the arm portion 1053 while the attachment cap 1070 remains essentially in place.

Once activated, the stored energy device 1030 will contact the carrier assembly, applying a force in a direction 1080 generally orthogonal to the major plane of the microneedle array 1052. This transfer of the application energy accelerates the carrier assembly in the direction of the skin, with the assembly eventually emerging through opening on the bottom of housing 1010. In certain embodiments, the central pedestal 1024 may continue to push the arm portion 1053 towards the skin, potentially resulting in increased penetration depth.

The geometry of the actuator 1020 can be adjusted such that the bottom face of the base 1021 is nearly in contact with the top surface of the upper housing at the time the stored energy device is actuated. In such an embodiment, the total distance that the housing 1010 can rebound away from the skin is limited due to the presence of a user's finger pushing down on the actuator 1020. Alternatively, the actuator 1020 can be designed to provide clearance between the bottom surface of the base 1021 and the top of the upper housing at the time of actuation, which would allow the housing 1010 to move a certain distance away from the skin as the stored energy device 1030 releases its potential energy.

Microneedle arrays suitable for use in the present disclosure may be used to deliver drugs (including any pharmacological agent or agents) through the skin in a variation on transdermal delivery, or to the skin for intradermal or topical treatment, such as vaccination.

In one aspect, drugs that are of a large molecular weight may be delivered transdermally. Increasing molecular weight of a drug typically causes a decrease in unassisted transdermal delivery. Microneedle arrays suitable for use in the present delivery systems have utility for the delivery of large molecules that are ordinarily difficult to deliver by passive transdermal delivery. Examples of such large molecules include proteins, peptides, nucleotide sequences, monoclonal antibodies, DNA vaccines, polysaccharides, such as heparin, and antibiotics, such as ceftriaxone.

In another aspect, microneedle arrays suitable for use in the present invention may have utility for enhancing or allowing transdermal delivery of small molecules that are otherwise difficult or impossible to deliver by passive transdermal delivery. Examples of such molecules include salt forms; ionic molecules, such as bisphosphonates, preferably sodium alendronate or pamedronate; and molecules with physicochemical properties that are not conducive to passive transdermal delivery.

In another aspect, microneedle arrays suitable for use in the present delivery system may have utility for enhancing delivery of molecules to the skin, such as in dermatological treatments, vaccine delivery, or in enhancing immune response of vaccine adjuvants. In one aspect, the drug may be applied to the skin (e.g., in the form of a solution that is swabbed on the skin surface or as a cream that is rubbed into the skin surface) prior to or after applying the microneedle array. In another aspect, the drug or fluid may be applied directly to the microneedles.

In another aspect, the delivery system may be used for creating microprotrusions in the skin.

The delivery systems may be used for immediate delivery, that is where they are applied and immediately removed from the application site, or they may be left in place for an extended time, which may range from a few minutes to as long as 1 week. In one aspect, an extended time of delivery may from 1 to 30 minutes to allow for more complete delivery of a drug than can be obtained upon application and immediate removal. In another aspect, an extended time of delivery may be from 4 hours to 1 week to provide for a sustained release of drug.

Objects and advantages of this invention are further illustrated by the following examples, but the particular materials and amounts thereof recited in these examples, as well as other conditions and details, should not be construed to unduly limit this invention. Unless otherwise indicated, all parts and percentages are by weight.

EXAMPLES

Two different fully assembled delivery systems were evaluated. For Example 1, a decoupled delivery system of the design described in FIGS. 1-5A-C and containing one spring was used. For Example 2, a decoupled delivery system of the design described in FIGS. 12-14 and containing three springs was used.

The housing components of the delivery systems were fabricated from ACCURA60 plastic (3D Systems, Rock Hill, S.C.) using a stereolithographic process. The external housing dimensions for Example 1 were 34.0 mm (diameter) by 9.4 mm (overall height). The opening in the housing for the array was 16.0 mm in diameter.

The external housing dimensions for Example 2 were 27.0 mm (diameter) by 8.0 mm (overall height excluding the actuator component). The opening in the housing for the array was 14.0 mm in diameter.

The bifurcated springs were four-legged domed springs (Snaptron, Windsor, Colo.) prepared from 301 full-hard stainless steel. As depicted in FIG. 6, the springs had a circular shape with four equally spaced and sized cut-out sections that were shaped as continuous arcs. For Example 1, the diameter (L1) of the springs was 20.2 mm. Each of the four leg regions formed by the cut-outs was 4.4 mm as measured along the outer edge of the leg (L2). The distance across and through the center of the springs at the narrowest point was 15.0 mm (L3). A 3.2 mm diameter hole was positioned in the center of the springs. The height of the domed springs before bifurcation and conditioning was 2.3 mm. The stock thickness of the domed springs before forming was 0.20 mm.

For Example 2, the diameter (L1) of the springs was 20.4 mm. Each of the four leg regions formed by the cut-outs was 3.9 mm as measured along the outer edge of the leg (L2). The distance across and through the center of the springs at the narrowest point was 13.7 mm (L3). A 3.2 mm diameter hole was positioned in the center of the springs. The height of the domed springs before bifurcation and conditioning was 1.8 mm. The stock thickness of the domed springs before forming was 0.18 mm.

Before placing the spring(s) in the assembly, the springs of Examples 1 and 2 were bifurcated and the activation energy level was set by the following spring conditioning process. The center of the single spring of Example 1 was displaced from its resting geometry at a rate of 0.1 mm/second through a bifurcation point until reaching a maximum displacement force of 3000 g after bifurcation. The spring was held at the maximum displacement force for 30 seconds before releasing the applied load. The targeted stored potential energy of the 1-spring system was 0.059 J. For Example 2, the center of each spring was displaced from its resting geometry at a rate of 0.1 mm/sec through a bifurcation point until reaching a maximum displacement force of 1500 g after bifurcation. Each spring was held at the maximum displacement force for 30 seconds before releasing the applied load. The targeted stored potential energy of the 3-spring system was 0.048 J.

For all examples, the spring conditioning procedures were designed to provide a spring or set of springs that produced a total targeted activation force of 350-400 g.

The flexible membrane in the delivery system of Example 1 was about 25.2 mm in diameter and was constructed from CoTran 9701 polyurethane film (3M Company, St. Paul, Minn.) having an initial film thickness of 2 mil. A film stretching procedure was used to create the bellowed membrane. The membrane was attached to both the lower housing (of an unassembled device) and the array carrier using a continuous coating of 3M Double Coated Medical Tape 1513 (3M Company, St. Paul, Minn.). The lower housing was simply supported at its perimeter and the membrane film was stretched by displacing the array carrier a distance of 12 mm at a rate of 0.5 mm/second and holding at its maximum displacement for 30 seconds. The assembly of the delivery system was completed by attaching the remaining components and positioning the now bellowed membrane with the attached array carrier in the cavity of the housing.

For Example 1, the microneedle array was molded as an integral portion of the array carrier using either LEXAN HPSIR-1125 polycarbonate (PC) (GE Plastics, Pittsfield, Mass.) or VECTRA MT 1300 thermoplastic liquid crystal polymer (LCP) (Ticona Engineering Polymers, Florence, Ky.). The microneedle array featured four-sided pyramidal shaped microneedles having heights of about 500 microns. Each microneedle was formed having a base width of about 167 microns and a tip width of about 10 microns. The microneedles were oriented in an octagon shaped pattern of about 471 microneedles with equal spacing between individual microneedles of about 550 microns (as measured from tip to tip). The array carrier featured a circular shaped base with a diameter of 13.4 mm.

For Example 2, the microneedle array was molded as an integral portion of the array carrier using LEXAN HPSIR-1125 polycarbonate (PC). The PC microneedle array featured four-sided pyramidal shaped microneedles having heights of about 250 microns. Each microneedle was formed having a base width of about 83 microns and a tip width of about 10 microns. The microneedles were oriented in an octagon shaped pattern of about 1288 microneedles with equal spacing between individual microneedles of about 275 microns (as measured from tip to tip). The array carrier featured a circular shaped base with a diameter of 12.7 mm. For Example 2, the array carrier also included an elongated arm 2.8 mm in diameter and 6.3 mm in length.

After actuation, the final resting position of the base of the microneedle array extended beyond the base of the lower housing by a distance of 0.11 mm for Example 1, and a distance of 0.08 mm for Example 2.

Microneedle Depth of Penetration Study

A study was conducted to determine the depth of penetration (DOP) of the microneedles of an array when applied to the skin surface of Yorkshire cross domestic pigs (Midwest Research Swine, Gibbon, Minn.), in vivo. Prior to application, the microneedle arrays were coated with Rhodamine B using a three-step coating process. In step one, the uncoated arrays were flood coated with a solution containing 50 µl of 1.0 mg/ml polyvinyl alcohol (80% hydrolyzed) (Sigma-Aldrich, St. Louis, Mo.) and 67 µg/ml of Tween® 80 (Sigma-Aldrich, St. Louis, Mo.) in 90% (weight/volume) ethyl alcohol. The coated arrays were dried at 35° C. for 20 minutes. In step two, the arrays were flood coated with 60 µl of an aqueous solution of 33.3 mg/ml aluminum potassium sulfate (Penta Manufacturing, Livingston, N.J.) and then dried at 35° C. for 30 minutes. In step three, the primed arrays were flood coated with 60 µl of an aqueous solution of 0.08% (weight/volume) Rhodamine B (Sigma-Aldrich, St. Louis, Mo.) and then dried at 35° C. for 30 minutes.

The ham area of the pig was selected as the application site. The ham area was first trimmed with an electric clipper followed by shaving with a razor and shaving cream. The ham was then rinsed with deionized water and wiped with 70/30 isopropanol water. The animals were anesthetized with isoflurane gas and maintained under anesthesia throughout the experiment.

A fully assembled delivery system as described for Example 1 was applied to the skin on the ham area of a pig with 3M Double Coated Medical Tape 1513. The delivery system was actuated, maintained on the animal for 15 minutes, and then removed.

The depth of penetration into the pig skin was determined indirectly by measuring the distance from the tip of the microneedle to where the Rhodamine B coating was wiped or dissolved from the microneedle after application into the skin. The measurement was conducted using a Nikon LV-100 microscope at 100× magnification (Nikon Instruments, Melville, N.Y.) with Image Pro® Plus digital image analysis software (Media Cybernetics, Bethesda, Md.). For each microneedle array type (PC or LCP), three animals were tested. The mean DOP was determined by sampling a subset of 72 microneedles from each array. Each array pattern was divided into four quadrants and relatively equal numbers of microneedles were sampled from each quadrant. In Table 1, the results are reported from the microneedle DOP study.

TABLE 1

Depth of Microneedle Penetration into Pig Skin

| Composition of Microneedle Array | Mean Microneedle Depth of Penetration (microns) | Standard Deviation (microns) | % RSD |
|---|---|---|---|
| PC | 113 | 14 | 12% |
| LCP | 141 | 42 | 30% |

Tetanus Toxoid Immunization Study

A fully assembled microneedle array delivery system as described in Example 2 was used in a tetanus toxoid immunization study.

The microneedle arrays described above were dip-coated (procedures to dip coating provided in United States Patent Application Publication No. US2008/0051699 (Choi, et al.)) with a formulation containing tetanus toxoid (Statens Serum Institute, Copenhagen, Denmark), sucrose (30%), hydroxyethyl cellulose (1%), and PBS buffer. The coated arrays were dried in an oven for 30 minutes at 35° C. The dried arrays were sealed in pouches with a foil-laminate moisture barrier and stored at 5±3° C. Prior to attaching to the assembly carrier, the arrays were equilibrated to ambient conditions (21° C. and 45% relative humidity). The coated arrays were attached to the array carriers of the delivery systems using 3M Double Coated Medical Tape 1513 at a time point of 3 hours or less before the start of the animal experiments.

A reverse phase HPLC assay was used to determine the tetanus toxoid content (in micrograms (mcg)) on the coated microneedle arrays. The dose of tetanus toxoid delivered to the animals was calculated by measuring the difference between the initial tetanus toxoid content on the arrays and the residual tetanus toxoid on the arrays after administration to the animals.

The male, hairless guinea pigs (obtained from Charles River Laboratories, Wilmington, Mass.) were approximately nine months old and weighed between 800 to 1000 g at the beginning of the study. A total of five animals were dosed on day 1 and on day 28 of the study. Anesthetized animals were dosed by attaching the fully assembled delivery system of Example 2 to the skin on the abdomen of the animal with 3M Double Coated Medical Tape 1513. The delivery system was actuated and maintained on the skin of the animal for 5 minutes. The mean value for the amount of tetanus toxoid coated on the arrays (mcg/array) and the mean calculated dose given to each animal (mcg/animal) is reported in Table 2. Approximately 50% of the tetanus toxoid coated on an array was delivered to the animal

TABLE 2

Mean Amount of Tetanus Toxoid

| | Mean Amount of Tetanus Toxoid Coated on an Array (n = 5) | Mean Amount of Teatanus Toxoid Dosed on Day 1 (n = 5) | Mean Amount of Teatanus Toxoid Dosed on Day 28 (n = 5) |
|---|---|---|---|
| Example 2 | 3.2 mcg/array | 1.6 mcg/animal | 1.5 mcg/animal |

Blood draws were conducted on anesthetized animals on days 28 and 56 of the study. The serum was separated and analyzed for anti-tetanus toxoid IgG using a mid-point tittering ELISA assay. The assay was standardized using NIBSC Code 98/572 Diptheria and Tetanus Antitoxin Guinea Pig Serum obtained from the National Institute for Biological Standards and Control (Hertfordshire, England). The anti-tetanus toxoid IgG titer was expressed in ELISA units with 20 ELISA units being equivalent to a measured IgG level of 0.2 IU/mL Animals with IgG titers greater than 20 ELISA units were determined to be seroconverted. In Table 3, the anti-tetanus toxoid IgG titer values on days 28 and 56 of the study are reported for each of the five animals. On day 28 (after one dose), three of the five animals were seroconverted. On day 56 (after two doses), all five animals were seroconverted.

TABLE 3

Anti-Tetanus Toxoid IgG Titer Values

| Animal Number | ELISA Units Measured Day 28 | Elisa Units Measured Day 56 |
|---|---|---|
| 1 | 19 | 167 |
| 2 | 67 | 678 |
| 3 | 106 | 1650 |
| 4 | 44 | 453 |
| 5 | 5 | 152 |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

We claim:

1. An integrated system for delivering a microneedle array, the system comprising:
   a housing having a height of at least 2 mm and no greater than 3.0 cm, a cavity therein, and including an applicator device;
   a carrier assembly including a solid microneedle array, wherein a portion of the carrier assembly is attached to the housing proximate the cavity and is in contact with a portion of the applicator; and wherein neither the carrier assembly nor the array are attached to the applicator device;
   a stored energy device comprising one or more bifurcating-springs that are capable of undergoing a shape change as a result of a predetermined force normal to a major plane of the stored energy device, wherein at least a portion of the stored energy device is located within the housing; and wherein the stored energy device can be actuated to apply force on the carrier assembly;
   wherein the applicator device further comprises an actuator; and
   wherein the actuator is movable within the housing in a certain direction orthogonal to the major plane of the stored energy device and the actuator comprises a screw received in a series of helical threads in the housing.

2. The integrated system of claim 1, wherein the carrier assembly comprises a flexible membrane.

3. The system of claim 2, wherein the membrane comprises a bellowed height greater than 500 microns and less than 1 cm.

4. The system of claim 3, wherein the membrane will not return to the bellowed height upon transfer of an application energy to the carrier assembly.

5. The system of claim 2, wherein the membrane is non-vented.

6. The system of claim 2, wherein the membrane comprises vents or apertures.

7. The system of claim 2, wherein the membrane comprises a polymeric film.

8. The system of claim 2, wherein the membrane comprises a sterilizable material.

9. The system of claim 1, wherein the height of the cavity is at least 550 microns and no greater than 2.0 cm.

10. An integrated system for delivering a microneedle array, the system comprising:
    a housing having a cavity therein and including an applicator device, the applicator device comprising an actuator comprising a screw received in a series of helical threads in the housing;
    a carrier assembly including a solid microneedle array, wherein a portion of the carrier assembly is attached to the housing proximate the cavity and is in contact with a portion of the applicator; and wherein neither the carrier assembly nor the array are attached to the applicator device; and
    a stored energy device comprising one or more bifurcating springs that are capable of undergoing a shape change as a result of a predetermined force normal to a major plane of the spring, wherein at least a portion of the stored energy device is located within the housing; and wherein the stored energy device can be actuated to apply force on the carrier assembly;
    wherein the actuator is movable within the housing in a certain direction orthogonal to the major plane of the stored energy device.

11. The integrated system of claim 10, wherein the carrier assembly comprises a flexible membrane.

12. The system of claim 11, wherein the membrane comprises a bellowed height greater than 500 microns and less than 1 cm.

13. The system of claim 12, wherein the membrane will not return to the bellowed height upon transfer of an application energy to the carrier assembly.

14. The system of claim 11, wherein the membrane is non-vented.

15. The system of claim 11, wherein the membrane comprises vents or apertures.

16. The system of claim 11, wherein the membrane comprises a polymeric film.

17. The system of claim 11, wherein the membrane comprises a sterilizable material.

18. The system of claim 10, wherein the actuator is slidably coupled to the housing.

19. The system of claim 10, wherein the height of the cavity is at least 550 microns and no greater than 2.0 cm.

20. The system of claim 10, wherein the height of the housing is at least 2 mm and no greater than 3.0 cm.

21. An integrated system for delivering a microneedle array, the system comprising:
    a housing having a cavity therein and including an applicator device comprising an actuator;
    a carrier assembly including a solid microneedle array, wherein a portion of the carrier assembly is attached to the housing proximate the cavity and is in contact with a portion of the applicator; and wherein neither the carrier assembly nor the array are attached to the applicator device; and
    a stored energy device comprising one or more bifurcating springs that are capable of undergoing a shape change as a result of a predetermined force normal to a major plane of the spring, wherein at least a portion of the stored energy device is located within the housing; and wherein the stored energy device can be actuated to apply force on the carrier assembly;
    wherein the actuator comprises a cam proximate to a surface of the stored energy device and rotatable to direct energy to the stored energy device.

22. The integrated system of claim 21, wherein the carrier assembly comprises a flexible membrane.

23. The system of claim 22, wherein the membrane comprises a bellowed height greater than 500 microns and less than 1 cm.

24. The system of claim 23, wherein the membrane will not return to the bellowed height upon transfer of an application energy to the carrier assembly.

25. The system of claim 22, wherein the membrane is non-vented.

26. The system of claim 22, wherein the membrane comprises vents or apertures.

27. The system of claim 22, wherein the membrane comprises a polymeric film.

28. The system of claim 22, wherein the membrane comprises a sterilizable material.

29. The system of claim 21, wherein the height of the cavity is at least 550 microns and no greater than 2.0 cm.

30. The system of claim 21, wherein the height of the housing is at least 2 mm and no greater than 3.0 cm.

31. An integrated system for delivering a microneedle array, the system comprising:
    a housing having a height of at least 2 mm and no greater than 3.0 cm, a cavity therein, and including an applicator device;
    a carrier assembly including a solid microneedle array, wherein a portion of the carrier assembly is attached to the housing proximate the cavity and is in contact with a portion of the applicator; and wherein neither the carrier assembly nor the array are attached to the applicator device;
    a stored energy device comprising one or more bifurcating-springs that are capable of undergoing a shape change as a result of a predetermined force normal to a major plane of the stored energy device, wherein at least a portion of the stored energy device is located within the housing; and wherein the stored energy device can be actuated to apply force on the carrier assembly; and
    wherein the actuator is slidably coupled to the housing and comprises a planar surface and one or more elongated posts, wherein at least one of the posts is received in a recess in the housing, and wherein at least one post is operable to contact the stored energy device when an activation force is applied to the planar surface.

32. The integrated system of claim 31, wherein the carrier assembly comprises a flexible membrane.

33. The system of claim 32, wherein the membrane comprises a bellowed height greater than 500 microns and less than 1 cm.

34. The system of claim 33, wherein the membrane will not return to the bellowed height upon transfer of an application energy to the carrier assembly.

35. The system of claim 32, wherein the membrane is non-vented.

36. The system of claim 32, wherein the membrane comprises vents or apertures.

37. The system of claim 32, wherein the membrane comprises a polymeric film.

38. The system of claim 32, wherein the membrane comprises a sterilizable material.

39. The system of claim 31, wherein the applicator device further comprises an actuator.

40. The system of claim 31, wherein the height of the cavity is at least 550microns and no greater than 2.0 cm.

* * * * *